United States Patent [19]

Bu'lock et al.

[11] Patent Number: 5,008,383

[45] Date of Patent: Apr. 16, 1991

[54] SURFACE-ACTIVE AGENTS

[75] Inventors: John D. Bu'lock; James K. Sutherland, both of Manchester; Michael J. Donnelly, Coventry, all of United Kingdom

[73] Assignee: 31 Research Exploitation Limited, London, England

[21] Appl. No.: 263,775

[22] PCT Filed: Apr. 9, 1987

[86] PCT No.: PCT/GB87/00243

§ 371 Date: Nov. 3, 1988

§ 102(e) Date: Nov. 3, 1988

[87] PCT Pub. No.: WO87/06236

PCT Pub. Date: Oct. 22, 1987

[30] Foreign Application Priority Data

Apr. 12, 1986 [GB] United Kingdom ............... 8608960

[51] Int. Cl.$^5$ .................. C07H 13/06; C07H 15/12; C07C 69/716; B01F 17/00
[52] U.S. Cl. ............................. 536/4.1; 260/410.8
[58] Field of Search ................... 536/4.1; 260/410.8

[56] References Cited

U.S. PATENT DOCUMENTS 3,214,461 10/1965 Elam et al. ................... 260/410.8

Primary Examiner—Ronald W. Griffin
Attorney, Agent, or Firm—Nixon & Vanderhye

[57] ABSTRACT

Novel surface-active compositions are prepared by reacting a diketene prepared from a fatty acid or fatty acid chloride with 8–22 carbon atoms with a substance having a hydrophlic moiety and a hydroxyl or amino group containing one or more active hydrogens. The active hydrogen-containing group is acylated by the diketene and the resulting product contains the hydrophillic moiety and also branched 2-alkyl-3-ketoacyl chains.

15 Claims, No Drawings

SURFACE-ACTIVE AGENTS

This invention relates to novel surface active compositions and to a process for their preparation.

It is already known that certain bacteria when cultivated under suitable conditions will produce useful surface active substances. Some of the most active of these bio-surfactants are exemplified by trehalose 6,6'-corynemycolate (which has formula I shown below), and are glycolipids having a hydrophilic moiety which is a sugar, which is esterified by hydrophobic components namely one or more fatty acids, the latter being of a particular type, that is, acids with double alkyl chains, constituted by the attachment of a second long alkyl chain at the 2-position of a long alkyl fatty acid; and either or both alkyl chains may carry other substituents or functional groups such as hydroxyl groups or centres of unsaturation.

Bio-surfactants of this type are known to show many desirable properties, and have been advocated as emulsification and wetting agents with potentially wide applications (as for instance by D. Gutnick, World Biotechnology Report (Biotech 84 U.S.A.), 1984, Volume 2, pp 645-652). Typically such bio-surfactants will lower the surface tension of aqueous salt solutions to ca. 30 dynes/cm at an air interface, or ca. 1-8 dynes/cm at an oil interface, and show critical micelle concentrations as low as 0.02 to 0.0002% w/w. However their production on an industrial scale by means of microbial cultures (as for instance might follow from studies such as described by Rapp, Bock, Wray & Wagner, J. Gen. Microbiol. 115, 491(1979)) is not likely to be very practical or economic because of generally low yields and technical difficulties in the fermentation and recovery processes (Parkinson, Biotechnology Advances 3, 65-83 (1985)).

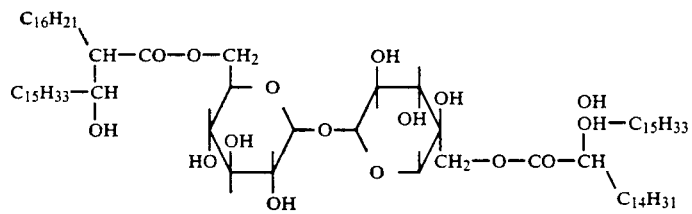
(I)

Equally there exist several well-known industrial routes whereby surface-active sugar esters may be commercially produced but, when using readily-available sugars and readily-available fatty acid derivatives, by such routes it has not hitherto been possible to produce sugar ester similar to (I), that is, with double alkyl chains as already described.

Specific chemical syntheses of (I) or related substances have been described, as for instance by Bottle and Jenkins, J. Chem. Soc. Chem. Commun. 1984, p385, or earlier workers, but they comprise several stages, are generally laborious, and are not such as to offer any commercially practicable route for the economic production of such substances.

An object of the present invention is to provide a process whereby novel useful surface active compositions comprising substances having double alkyl chains can be prepared in a simple and convenient manner.

According to the present invention there is provided a process for the preparation of a surface-active substance having the general formula

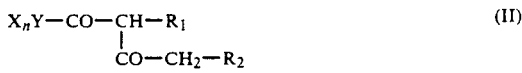

wherein;
each of $R_1$ and $R_2$, which may be the same or different, is an alkyl chain having from 6 to 20 carbon atoms;
X is a mono- or di-valent hydrophilic moiety;
n is 1 or 2; and,
Y is $-CH_2O-$ or $-NH-$ or

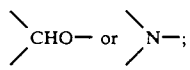

said process comprising reacting a compound of the general formula

in which X, Y and n are as defined hereinabove, with a diketene of the general formula III or IV;

wherein $R_1$ and $R_2$ are as stated above, so that the group YH is acylated by the diketene, the acylation reaction being carried out in the presence of a non-acylable nitrogenous base as proton acceptor catalyst and in a polar aprotic solvent medium.

The non-acylable nitrogenous base may be a tertiary amine or a pyridine or a tertiary amino pyridine derivative.

Preferably, the said alkyl chains $R_1$ and $R_2$ are unbranched and contain no more than three double bonds.

Preferably, the said alkyl chains $R_1$ and $R_2$ are at least substantially unbranched and contain from 0 to 3 double bonds.

It is to be understood that the process of the invention may result in a composition which comprises a single surface-active substance, and the or each such substance may have one or a plurality of acylated groups.

In performing the process of the invention diketenes [ketene dimers, formulae (III), (IV)] are used which can be readily and efficiently obtained from common fatty acids (as for instance described in standard texts such as S. Patai (editor), "The Chemistry of Ketenes, Allenes and Related Compounds", Wiley 1980) and the invention is based on the realisation that these can be used to acylate suitable sugars or sugar derivatives or other hydrophilic substances and that, if the common fatty acids from which the ketene dimers are prepared have from eight to twenty-two carbon atoms, the products of the acylation may be useful, effective, and efficient surface-active agents. Acylation by such ketene dimers is capable of yielding products in which the hydrophilic entities are esterified with branch-chain 2-alkyl-3-keto-acyl groups, as in formula (II). These provide double alkyl chain structures similar to those exemplified in the above bio-surfactant (I), except that a 3-keto-group replaces the 3-hydroxyl-groups in the hydrophobic moieties. The acylation products may moreover be chemically converted by simple further steps into other useful surface-active agents having double alkyl chains.

The process of the invention can be easily carried out with high yields. Although the resulting products may include products similar to (I), in general they are obtainable more easily, and in greater variety, than the microbial products described above, particularly since the nature of the hydrophilic component may be more freely selected and the overall proportion of hydrophilic to hydrophobic residues in the products can be more readily selected to meet requirements.

The acylation reaction of the process of the invention may be performed as a second step following a first step in which the ketene dimers are formed and this may be necessary or desirable if the requisite dimers are not readily commercially available. If desired, the two steps may be conducted by successive operations in a single vessel. The first step may involve procedures already well known for the conversion of a fatty acid chloride into the corresponding ketene dimer, which may be a compound of either type (III) or type (IV), or a mixture of the two, in which the alkyl groups $R_1$, $R_2$ derive from the original fatty acid chloride (e.g. an acid chloride $R_1.CH_2.CO.Cl$ gives the alkyl group $R_1$), depending on reaction and work-up conditions. The fatty acid chloride may be derived from an n-alkyl-carboxylic acid containing eight to twenty-two carbon atoms, which may or may not contain other structural features such as centres of unsaturation in the alkyl chain, or from a mixture of such acids as obtained by the hydrolysis of common triglycerides, and more particularly an acid chloride or mixture of acid chlorides such as tetradecanoyl, hexadecanoyl or octadecanoyl chloride. The conversion of the acid chloride into the ketene dimer or dimers may be carried out by various well-known means but for the present purposes it is preferable to carry it out by means which allow the crude product of the reaction, for example as obtained by conventional removal of a volatile solvent, to be used directly without intermediate purification.

In the acylation reaction of the invention which may be a second step as described above, the ketene dimer is reacted with a suitable sugar or other hydrophilic substance. For this reaction a basic catalyst is to be used, which will act as a proton acceptor, and the combination of basic catalyst, solvent and reaction conditions used should be such as will not promote competing unwanted reactions such as decomposition of the ketene dimer or the hydrophilic substance.

A suitable hydrophilic substance for use in the process of the invention is one which contains groups that will enter into the acylation reaction with the ketene dimer, together with further hydrophilic (that is, polar) groups such that the whole structure will furnish the eventual acylation product with a hydrophilic moiety. Suitable substances for this purpose may be compounds with a multiplicity of hydroxyl groups such as sugar derivatives, hydroxy-amines with a similar multiplicity of hydroxyl and amino-groups, or hydroxy- or amino-polyethers such as polyoxy- or polyamino-alkylenes.

Suitable sugar substances include mono-saccharides, such as glucose, or di-saccharides, such as sucrose or oligosaccharides, or poly-saccharides such as a dextran, or sugar alcohols or polyols such as sorbitol, or sugar derivatives such as a glucoside particularly a methyl glucoside, or a derivative containing other functional groups as in sugar derivatives containing one or more NH groups such as a N-methyl-1-amino-1-deoxy-glucose or as in a sugar previously subjected to oxyalkylation or polyoxyalkylation by standard means such as a sugar derivative containing one or more hydroxyalkoxy- or hydroxyalkoxy-polyalkoxy substituents, or a mixture or such substances. Further examples of suitable hydrophilic substances include hydrophilic non-sugars containing appropriate functionalities, such as a polyoxyalkylene glycol or a poly-hydroxyalkylamine.

For the reaction to proceed it is simply and particularly necessary for the sugar or other hydrophilic substance to contain reactive hydrogen in the form of hydroxyl groups such as

groups or more particularly —$CH_2OH$ groups, or similar nucleophilic centres such as —$NH_2$ or

groups, such groups being comparatively readily acylated. For the hydrophilic component to be suitable for the preparation of a useful surfactant by this process it will normally be the case that more than one such group is present in the hydrophilic component, and the extent of the acylation process may then be controlled by controlling the reaction conditions and especially by controlling the molar proportion of ketene dimer to hydrophilic component, which is preferably approximately one mole per molar proportion of the desired acylable group.

The above mentioned basic catalyst used for the reaction may be a tertiary nitrogenous base such as a trialkylamine or pyridine or N-methylmorpholine or an N-alkylpyrrolidine or a 4-N'N'-dialkylamino-pyridine, and it is supplied preferably in the proportion of from 0.05 to 0.5 moles of base per mole of ketene dimer and more especially from 0.05 to 0.10 moles.

The acylation reaction is facilitated by conducting the conversion in the absence of significant amounts of water and in a suitable polar but essentially aprotic solvent such as dimethylformamide or dimethylsuphoxide, and where the reactants are not fully soluble in such a solvent the reaction may be facilitated by creating a microdispersion of the reactants in the solvents by well-known means such as sonic vibration.

The reaction is preferably carried out at a temperature of from 45° to 150° C. and more especially from 50° to 95° C.

The required duration of the reaction in any particular instance can be ascertained by well-known analytical methods applied to samples withdrawn from the reaction mixture and in typical instances it may be between six and 48 hours.

The product of the reaction is typically a waxy solid and is obtained by conventional removal and recovery of solvent and residual catalyst. Its subsequent purification is optional and depends on the technical use to which the product is to be applied. In typical procedures the yield of reaction product on a molar basis from the ketene dimer is over 50% and normally at least 75% of the partly-purified products.

Typical products from this reaction sequence may be effective and efficient surface-active agents, superior to some synthetic surfactants and approaching the performance ascribed to typical bio-surfactants. This is indicated in Table 1, which shows for several such products (prepared in accordance with Examples 1 to 3 described hereinafter) the critical micelle concentration, as a measure of surfactant efficiency, the surface tensions at air-water and oil-water interfaces measured at the critical micelle concentration, as measures of surfactant effectiveness. For the purpose of comparison, Table 1 also shows some corresponding data for three well-known products, namely a synthetic sodium alkylbenzene sulphonate, a commercially-available sucrose n-alkyl fatty acid ester, and the bacterial glycolipid (I).

Moreover the products from this reaction sequence, being esters or amides of 2-alkyl-3-keto-acids, may be further converted by well-known reactions involving the carbonyl function of the 3-keto-group into further substances such as the corresponding 2-alkyl-3-hydroxyl-derivatives, or the 2-alkyl-2,3-unsaturated derivatives or the 2-alkyl-derivatives, and the 2-alkyl-3-hydroxy-derivatives may be further converted into 3-0-substituted derivatives. Such conversions may be useful as affording products with particular modifications of the surface activity properties.

The invention will now be described further in the following Examples.

EXAMPLE 1

Stearoyl chloride (75.0 g, 0.24 moles) and dichloromethane (720 cm$^3$, distilled and dried) were charged to a flask (1 liter) equipped with a magnetic stirrer. Triethylamine (26.1 g, 0.258 moles) was added to the agitated solution over approximately 30 seconds causing a slight rise in temperature which rapidly dissipated. The mixture was agitated at room temperature in the sealed flask. Periodically agitation was stopped temporarily, the precipitate allowed to settle, and the clear upper solution sampled (approximately 0.5 cm$^3$) for IR spectroscopy. The reaction was followed by measurement of the peak height of the absorption at 1800–1805 cm$^{-1}$; after the peak height became relatively constant (23 hours) the CH$_2$Cl$_2$ was evaporated under vacuum (approximately 8 mm).

The pale yellow residue (101 g) was dissolved in distilled hexane (430 cm$^3$) and the precipitate of triethylamine hydrochloride filtered off and washed with hexane. The combined filtrates were evaporated to dryness under vacuum (approximately 8 mm) to yield a pale yellow liquid which solidfied at room temperature (65.9 g, mp=50°–51° C., calculated for C$_{36}$H$_{68}$O$_2$: C=81.2%; H=12.8%; found: C=78.6%; H=12.9%; tlc Rf=0.71; UV max=215 nm, log E max=2.85). Spectroscopic measurements confirm the crude product as consisting substantially of 3-hexadecyl-4-hepta-decylidenyl-butyrolactone (above, (III), (IV), R$_1$=R$_2$=C$_{16}$H$_{33}$), the ketene dimer. The ketene dimer (60 g, 0.11 moles), anhydrous sucrose (20 g, 0.06 moles), 4-dimethylamino-pyridine (0.69 g, 0.0006 moles) and dry dimethylformamide (1.5 liters) were heated together with stirring at 95° C. for 21 hours after which time the solvent was removed under reduced pressure. Non-polar components were removed by hexane extraction of the concentrated dimethylformamide solution followed by final evaporation of solvent to give the final crude product in 65% yield. Spectroscopic analyses indicated that this product, for which some data are given in Table 1, was a mixture of mono- and di-ketoacyl esters of sucrose. The molar ratio of hydrophilic component (sucrose) to ketene dimer was 0.5.

EXAMPLE 2

Equimolar amounts of the diketene (6 g) prepared as in Example 1 but from tetradecanoyl chloride, and 1-methylamino-1-deoxyglucose (2.2 g) prepared according to the procedure described in Ger. Offen. No. 2,832,127 Chemical Abstracts 90:204428p) were reacted in dry dimethylformamide (50 ml) with stirring at 80° C. for 20 hours; the reaction mixture was cooled and extracted with several 20 ml lots of hexane.

The combined hexane extracts were evaporated under reduced pressure to give the product (5.5 g) for which some data are reported in Table 1, and which from spectroscopic measurements contains the N-ketoacyl-derivative of 1-methylamino-1-deoxyglucose as the principal component. The molar ratio of hydrophilic component (glucose derivative) to ketene dimer was 1.0.

EXAMPLE 3

Using the conditions and procedure described in Example 1, the ketene dimer (58 g) obtained as in Example 1 and anhydrous sorbitol (20 g) were reacted together with 4-dimethylaminopyridine in dimethyl-formamide. The hexane-insoluble product fraction (49 g) was shown by spectroscopic analysis to consist almost entirely of the I-(3-ketoacyl) ester of sorbitol, and some data for this product are shown in Table 1. The molar ratio of hydrophilic component (sorbitol) to ketene dimer was 1.0.

TABLE 1

| | Surface Active Composition | Critical micelle concentration (CMC) (w/w %) |
|---|---|---|
| 1. | Product of Example 1 | 0.00005 |
| 2. | Product of Example 2 | 0.001 |
| 3. | Product of Example 3 | 0.0009 |
| 4. | Sodium monoalkylbenzene sulphonate (Data source - European Symposium on Enhanced Oil Recovery, Edinburgh 1978) | 0.003 |
| 5. | Sucrose ester, commercial (Data source - Croda F.50) | 0.01 |
| 6. | Glycolipid (I) (Data source - Wagner et al, 1984: 3rd Eur. Congr. Biotechnol, Munich Abstr. 1.3–1.8) | 0.0002 |

Surface tension measured at CMC (dyne/cm)

TABLE 1-continued

|   | Air/Water | Air/aq. salts | Oil/aq. salts |
|---|---|---|---|
| 1. | 21.0 | 21.0 | 7.0 |
| 2. | 21.0 | 22.0 | 7.0 |
| 3 | 26.0 | 29.0 | 12.0 |
| 4. | — | — | 0.7 |
| 5. | — | 18.5 | 9.5 |
| 6. | — | 36.0 | 17.0 |

We claim:

1. A process for the preparation of a surface-active substance having the formula

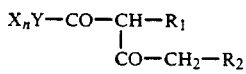  (II)

wherein;
each of $R_1$ and $R_2$, which may be the same or different, is an alkyl chain having from 6 to 20 carbon atoms;
X is a mono- or di-valent hydrophilic moiety;
n is 1 or 2; and,
Y is $-CH_2O-$ or $-NH-$ or

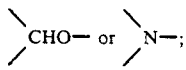

said process comprising reacting a compound of the formula

in which X, Y and n are as defined hereinabove, with a diketene of the formula III or IV;

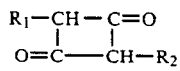  (III)

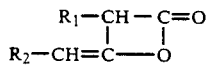  (IV)

wherein $R_1$ and $R_2$ are as stated above, so that the group YH is acylated by the diketene, the acylation reaction being carried out in the presence of a non-acylable nitrogenous base as proton acceptor catalyst and in a polar aprotic solvent medium.

2. A process according to claim 1, wherein the non-acylable nitrogenous base is a tertiary amine or a pyridine or a tertiary amino pyridine derivative.

3. A process according to claim 1 or claim 2 wherein the said alkyl chains have 8 to 22 carbon atoms, are unbranched and also contain centers of unsaturation having no more than three double bonds.

4. A process according to claim 1, wherein the diketene is derived from one or more n-alkyl fatty acids and/or one or more n-alkyl acid chlorides, the fatty acid or acid chloride containing 8 to 22 carbon atoms.

5. A process according to claim 4, wherein the diketene is prepared from an n-alkyl acid chloride and is used as acylating agent containing the hydrophilic moiety without purification.

6. A process according to claim 1, wherein the said compound containing the hydrophilic moiety is selected from mono-saccharides, di-saccharides, oligosaccharides, polysaccharides, sugar alcohols, polyols, glycosides, sugar derivatives containing one or more NH groups, sugar derivatives containing one or more hydroxyalkoxy- or hydroxyalkoxy- polyalkoxy substituents, polyoxyalkylene glycols, poly- hydroxyalkylamines and mixtures thereof.

7. A process according to claim 1, wherein the diketene is prepared from n-alkyl acid chloride and is used to acylate the said compound containing the hydrophilic moiety without purification.

8. A surface-active compound having the formula:

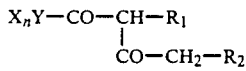

wherein
$R_1$ is an alkyl chain having from 6 to 20 carbon atoms;
$R_2$ is an alkyl chain having from 6 to 20 carbon atoms the same as or different from $R_1$;
X is a mono- or di-valent hydrophilic moiety;
n is 1 or 2; and
Y is $-CH_2O-$ or $-NH-$ or

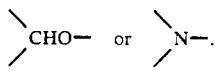

9. A surface-active composition comprising a carrier or diluent and a surface-active substance having the formula:

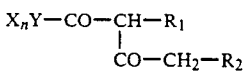

wherein
$R_1$ is an alkyl chain having from 6 to 20 carbon atoms;
$R_2$ is an alkyl chain having from 6 to 20 carbon atoms the same as or different from $R_1$;
X is a mono- or di-valent hydrophilic moiety;
n is 1 or 2; and
Y is $-CH_2O-$ or $-NH-$ or

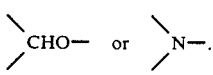

10. A surface active substance prepared by the process of claim 1.

11. A surface active substance prepared by the process of claim 2.

12. A surface active substance prepared by the process of claim 3.

13. A surface active substance prepared by the process of claim 4.

14. A surface active substance prepared by the process of claim 5.

15. A surface active substance prepared by the process of claim 6.

* * * * *